United States Patent
McFann et al.

(12) 
(10) Patent No.: US 6,406,442 B1
(45) Date of Patent: Jun. 18, 2002

(54) GUIDEWIRE FOR PRECISION CATHETER POSITIONING

(75) Inventors: Timothy B. McFann, Redwood City; John C. Muskivitch, Cupertino; James D. Passafaro, Los Gatos; Kathy M. Mah, Mountain View, all of CA (US)

(73) Assignee: Prolifix Medical, Inc., Sunnyvale, CA (US)

( * ) Notice: Subject to any disclaimer, the term of this patent is extended or adjusted under 35 U.S.C. 154(b) by 0 days.

(21) Appl. No.: 09/289,850

(22) Filed: Apr. 12, 1999

Related U.S. Application Data

(63) Continuation-in-part of application No. 08/966,001, filed on Nov. 7, 1996, now Pat. No. 6,156,046.
(60) Provisional application No. 60/103,447, filed on Oct. 7, 1998, provisional application No. 60/081,614, filed on Apr. 13, 1998, and provisional application No. 60/081,631, filed on Apr. 13, 1998.

(51) Int. Cl.$^7$ .................................................. A61B 5/00
(52) U.S. Cl. ........................................ 600/585; 600/434
(58) Field of Search ................................ 600/433, 434, 600/435, 585

(56) References Cited

U.S. PATENT DOCUMENTS

| | | | |
|---|---|---|---|
| 4,706,671 A | 11/1987 | Weinrib | 606/159 |
| 4,732,154 A | 3/1988 | Shiber | 606/159 |
| 4,745,919 A | 5/1988 | Bundy et al. | 606/159 |
| 4,890,611 A | 1/1990 | Monfort et al. | 606/159 |
| 4,909,781 A | 3/1990 | Husted | 604/22 |
| 4,950,277 A | 8/1990 | Farr | 606/159 |
| 4,979,939 A | 12/1990 | Shiber | 606/159 |
| 5,007,896 A | 4/1991 | Shiber | 604/22 |
| 5,011,488 A | 4/1991 | Ginsburg | 606/159 |
| 5,030,201 A | 7/1991 | Palestrant | 604/22 |
| 5,047,040 A | 9/1991 | Simpson et al. | 606/159 |

(List continued on next page.)

FOREIGN PATENT DOCUMENTS

| | | |
|---|---|---|
| EP | 0448859 | 10/1991 |
| EP | 0254414 | 8/1992 |
| EP | 0501772 | 9/1992 |
| EP | 0360791 | 8/1994 |
| EP | 0337918 | 11/1994 |
| EP | 0421457 | 1/1995 |
| EP | 0379786 | 3/1995 |
| EP | 0680730 | 11/1995 |
| EP | 0442137 | 2/1996 |
| WO | WO 82/04388 | 12/1982 |
| WO | WO 89/00835 | 2/1989 |
| WO | WO 94/04081 | 3/1994 |
| WO | WO 94/10919 | 5/1994 |
| WO | WO 95/27443 | 10/1995 |
| WO | WO 96/39084 | 12/1996 |

*Primary Examiner*—Cary O'Connor
*Assistant Examiner*—Charles Marmor, II
(74) *Attorney, Agent, or Firm*—Townsend and Townsend and Crew LLP

(57) ABSTRACT

The present invention comprises a guidewire having a compressible guide section capable of deflecting a catheter to abut a lumen wall. The compressible guide section exerts an outward radial force while it is at least partially compressed within a lumen. The guide section permits a physician to precisely locate a catheter within a body lumen and adjust a catheter tip orientation to be directed to a particular side of a body lumen. A method is disclosed for properly matching a guidewire and a catheter to operate together in the present invention, along with a force measuring instrument to assist in measuring a catheter's resistance force value. This method and systems of the present invention involve determining the exact force relationship between the compressible guide section and the resistance of the catheter in vitro.

3 Claims, 6 Drawing Sheets

U.S. PATENT DOCUMENTS

| | | | |
|---|---|---|---|
| 5,054,501 A | 10/1991 | Chuttani et al. | 600/585 |
| 5,078,722 A | 1/1992 | Stevens | 606/159 |
| 5,078,723 A | 1/1992 | Dance et al. | 606/159 |
| 5,100,423 A | 3/1992 | Fearnot | 606/159 |
| 5,116,352 A | 5/1992 | Schnepp-Pesch et al. | 606/171 |
| 5,131,407 A * | 7/1992 | Ischinger et al. | 600/585 |
| 5,135,531 A | 8/1992 | Shiber | 606/159 |
| 5,143,085 A | 9/1992 | Wilson | 600/585 |
| 5,158,564 A | 10/1992 | Schnepp-Pesch et al. | 606/159 |
| 5,195,954 A | 3/1993 | Schnepp-Pesch et al. | 604/22 |
| 5,224,945 A | 7/1993 | Pannek, Jr. | 606/159 |
| 5,251,640 A | 10/1993 | Osborne | 600/585 |
| 5,269,751 A | 12/1993 | Kaliman et al. | 604/22 |
| 5,306,244 A | 4/1994 | Shiber | 604/510 |
| 5,306,252 A | 4/1994 | Yutori et al. | 600/585 |
| 5,314,407 A | 5/1994 | Auth et al. | 604/22 |
| 5,314,438 A | 5/1994 | Shturman | 606/159 |
| 5,318,576 A | 6/1994 | Plassche, Jr. et al. | 606/159 |
| 5,320,634 A | 6/1994 | Vigil et al. | 606/159 |
| 5,334,211 A | 8/1994 | Shiber | 606/159 |
| 5,356,418 A | 10/1994 | Shturman | 606/418 |
| 5,360,432 A | 11/1994 | Shutrman | 606/159 |
| 5,402,799 A | 4/1995 | Colon et al. | 600/585 |
| 5,403,334 A | 4/1995 | Evans et al. | 606/159 |
| 5,409,015 A | 4/1995 | Palermo | 600/585 |
| 5,417,703 A | 5/1995 | Brown et al. | 606/159 |
| 5,443,443 A | 8/1995 | Shiber | 604/22 |
| 5,465,733 A * | 11/1995 | Hinohara et al. | 600/585 |
| 5,480,382 A * | 1/1996 | Hammerslag et al. | 604/528 |
| 5,490,859 A | 2/1996 | Mische et al. | 606/159 |
| 5,501,694 A | 3/1996 | Ressemann et al. | 606/159 |
| 5,514,115 A | 5/1996 | Frantzen et al. | 604/531 |
| 5,522,875 A | 6/1996 | Gates et al. | 607/127 |
| 5,527,326 A | 6/1996 | Hermann et al. | 606/159 |
| 5,540,707 A | 7/1996 | Ressemann et al. | 606/159 |
| 5,556,408 A | 9/1996 | Farhat | 606/180 |
| 5,569,277 A | 10/1996 | Evans et al. | 606/159 |
| 5,571,122 A | 11/1996 | Kelley et al. | 606/159 |
| 5,584,843 A | 12/1996 | Wulfman et al. | 606/159 |
| 5,596,996 A | 1/1997 | Johanson et al. | 600/585 |
| 5,616,149 A | 4/1997 | Barath | 606/159 |
| 5,620,451 A | 4/1997 | Rosborough | 606/108 |
| 5,622,188 A | 4/1997 | Plaia et al. | 128/898 |
| 5,643,298 A | 7/1997 | Nordgren et al. | 606/159 |
| 5,715,817 A * | 2/1998 | Stevens-Wright et al. | 600/373 |
| 5,876,414 A | 3/1999 | Straub | 606/159 |
| 5,904,657 A * | 5/1999 | Unsworth et al. | 600/585 |
| 6,086,548 A * | 7/2000 | Chaisson et al. | 600/585 |

* cited by examiner

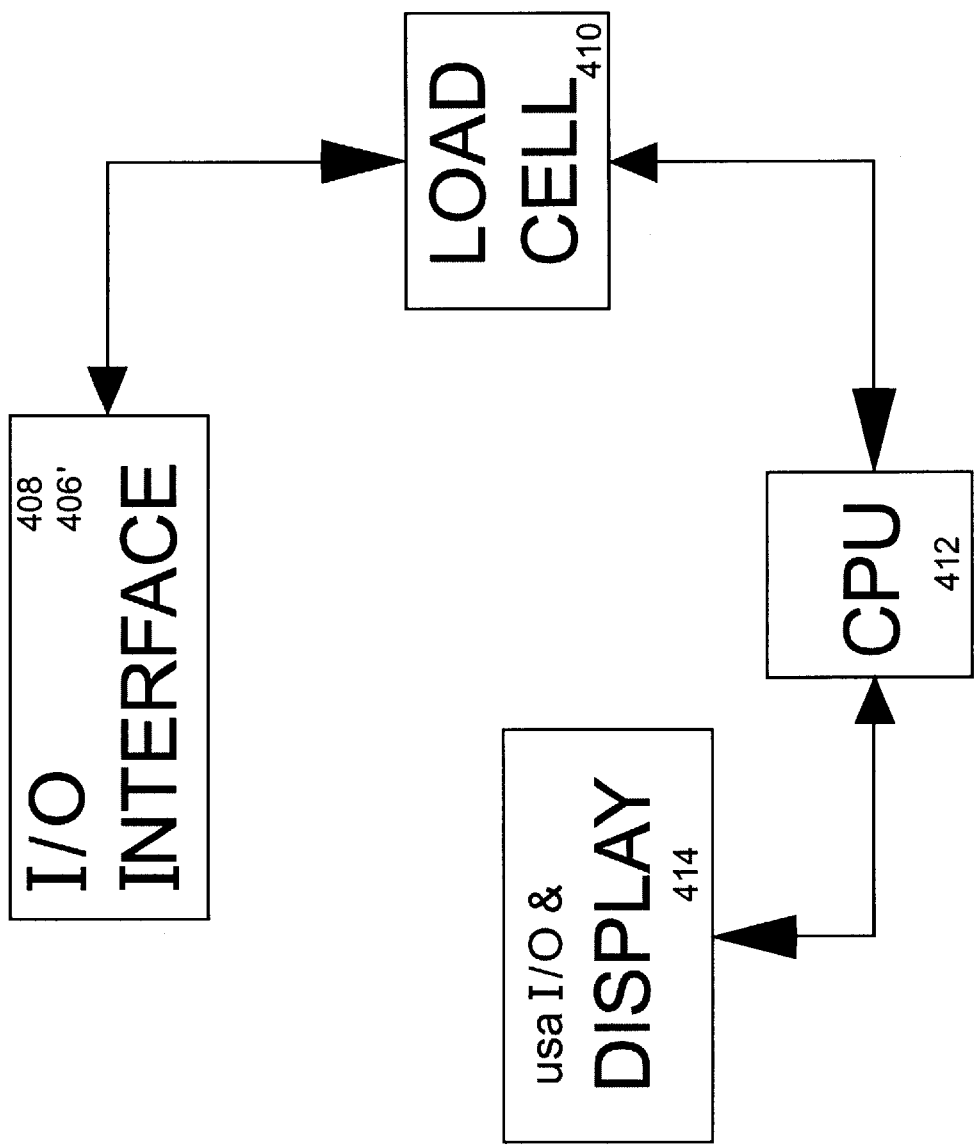

GUIDEWIRE FOR PRECISION CATHETER POSITIONING

CROSS-REFERENCES TO RELATED APPLICATIONS

This application is a continuation-in-part from U.S. Ser. No. 08/966,001 and filed Nov. 7, 1996—now U.S. Pat. No. 6,156,046 references and claims the benefit under 37 CFR §1.78 of U.S. Provisional Application No. 60/103,447 filed Oct. 7, 1998, U.S. Provisional Application No. 60/081,614 filed Apr. 13, 1998, and U.S. Provisional Application No. 60/081,631 filed Apr. 13, 1998, the full disclosures of which are herein incorporated by reference. This application is also related to co-pending U.S. Applications entitled "APPARATUS FOR MAKING WIRE WITH RADIAL EXPANSIBLE GUIDE SECTION AND METHODS OF MANUFACTURING THE SAME," Ser. No. 09/290,510 and "VARIABLE STIFFNESS CATHETER FOR THE TREATMENT OF A BODY LUMEN, SYSTEMS AND METHODS OF USING THE SAME," Ser. No. 09/289,849, filed on the same day as the present application, the full disclosures of which are incorporated herein by reference.

BACKGROUND OF THE INVENTION

1. Field of the Invention

The present invention relates generally to a guidewire for directing a medical device to a precise location within a body lumen, such as blood vessels. Methods are provided for properly matching a guidewire and catheter together for safe operation and precise location. In particular, the present invention relates to apparatus and methods for guided atherectomy.

2. Description of the Background Art

Medical guidewires are used primarily to facilitate the placement of catheters and endoscopic instruments within the tortuous paths of body conduits. For example, if it is desirable to place a catheter within the vascular system of a patient, a guidewire is first inserted into the vessel and then guided through the tortuous path desired for the catheter. Then the catheter is threaded over the guidewire. As the catheter is advanced it tends to follow the direction of the guidewire so that it ultimately negotiates the same tortuous path. Once the catheter is in its final operative position, the guidewire can be removed leaving the catheter to perform its desired function.

Guidewires are traditionally utilized to negotiate the complex vascular system of a patient to guide a medical device, (e.g. a catheter) to a desired location. It has been in the past of paramount importance for the guidewire to have a shape which provides for superior navigation a patient's vascular system. Inventions in the field include guidewires with floppy tips, improved methods of manufacturing, increased torquability and improved friction reducing features to help catheters move over the guidewires. Thus the focus of the prior art has been to create a guidewire with the ability to create a path along which a catheter could follow to reach a particular site of the body.

Guidewires often use transition areas of changing diameter along their length. A smooth transition gives the guidewire the ability to better negotiate tight bends in the anatomy of the patient. The transition area of a guidewire may be long or short, that is the change from one diameter along the length of the guidewire may occur over a few millimeters, or several centimeters. In the past the use of transition areas has been combined with the use of a filament wire which covers the narrower distal section of the guidewire. The combination, well understood in the art, provides the distal tip of the wire with a greater flexibility to steer through the vasculature of a patient, while the filament wire provides added strength and radiopacity. The filament wire can also be used as a fastening point for the attachment of an atraumatic tip. Examples of guidewires using the combination of transition areas and filament wires are described in Colon et al., (U.S. Pat. No. 5,402,799) and Ashby et al., (U.S. Pat. No. 5,622,184). Others have modified the basic design by using other materials, such as Johanson et al., (U.S. Pat. No. 5,596,996). However all of the prior art to date has used guidewires for essentially the same purpose, to navigate the anatomy of a patient and direct a catheter to a particular site within a body lumen. The medical procedure to be carried out is then conducted by the catheter. There are specialized guidewires which have been developed which attempt to do the job of a catheter using a modified guidewire. Two examples are guidewires with imaging and non-imaging sensors.

However there remains a need for a guidewire which can steer a catheter more particularly to a precise position within the vascular system of the patient. More particularly it would be beneficial to be able to manufacture a guidewire able to direct a catheter to a particular side of a lumen in the event a physician wishes to treat one side of a body lumen and not another, or be able to direct a catheter to precise locations of a body lumen. Straight guidewires are unable to perform this feat, however a novel guidewire has been disclosed in co-pending application Ser. No. 08/966,001 which is capable of steering catheters to a particular side of a body lumen. Furthermore, a method of determining the proper sizing of a medical device is desirable. At least some of these objectives will be met by the embodiments of the present invention described below.

SUMMARY OF THE INVENTION

The present invention relates to a guidewire for precise location of a medical device in a body lumen. A method for matching a guidewire of the present invention to a catheter is also provided. The guidewire of the present invention possesses a proximal end and a distal end with a compressible guide section comprising a plurality of helical winds located substantially at the distal end. Each helical wind of the guide section is capable of exerting an outward radial force when the guide section is compressed. The outward radial force is designed to exceed a catheter resistance force ($F_c$). The outward radial force the guide section exerts on the catheter ($F_{GS}$) is produced by the portion of the helical wind that is held off a lumen wall. The portion held off of the lumen wall is the length of the guide section between the distal tip of a catheter tracking over it, and the point at which the guide section makes contact with the lumen distal to the catheter distal tip.

The guide section may be made with helical winds, such as a regular circular coil, or a near helical series of shapes, such as a polygon having a no sharp corners that would interfere with a medical device tracking over it, or pose a health risk to a patient. The outward radial force per unit length of the entire guide section is generally less than 4 pounds per centimeter of unconstrained length, and the radial force for any portion used for precision location is less than 2 pounds. The force for precision location is preferably less than one half pound.

The compressible guide section is made of a shape memory material, such as a metal alloy like nickel-titanium.

Other materials may be used including ceramic composites or polymers provided the elastic and super-elastic strain of these materials is not exceeded during the actual use of the guidewire. The guide section may also be made from another low strain metal using a shape memory cladding. The guide section has sufficient outward radial force to overcome the inherent resistance force of either a standard over the wire catheter, or a rapid exchange (RX) catheter.

One alternative embodiment of the present invention is a guidewire having a proximal end, a distal end, and at least one displacement arm attached to the distal end. The displacement arm exerts an outward radial force when compressed. The displacement arm comprises a wire made of a shape memory alloy and operates similar to a single arc helical wind. The displacement arm anchors in the body lumen and deflects the guidewire tip into a lumen wall. Radiopaque markers provide a means for precision location of the wire in operation. The guidewire of this embodiment may have multiple displacement arms. When multiple displacement arms are used, the displacement arms preferably all have the same directional bias.

Another embodiment of the present invention comprises guidewire having a proximal end, a distal end and a lumen extending at least partially through said distal end. A filament wire is fixed to the interior distal tip of the guidewire. The filament wire is made from a shape memory material with a plurality of preformed curves. The guide section further comprises a plurality of apertures near the distal end of the guidewire. The preformed curves protrude through the apertures in the wire and act as spring detents for pushing the distal tip of the guidewire into the lumen wall. When a catheter tracks over the guide section and across the apertures, the filament wire compresses and lays completely within the filament wire lumen of the guide section. The spring detents are designed to "straddle" the length of a rapid exchange catheter tracking over the distal end of the guidewire. By forming spring detents on either side of a rapid exchange catheter, the guide section of the guidewire is forced to abut the lumen wall.

A portable force resistance meter is also disclosed for determining a catheter's force resistance value. The force resistance meter comprises an aperture for receiving a catheter distal tip, a deflection lever for moving said catheter distal end a quantifiable distance, a load cell linked to said deflection lever, a microprocessor and a display unit. The microprocessor may be programmed to display an appropriate matching guidewire for the catheter tested.

A method for determining the outward radial force a compressible guide section exerts can be determined following the steps of: incrementally axially displacing the guide section using a force-displacement measuring device, recording the axial force and axial and radial displacement at each increment, calculating the outward radial force from these measured values.

A method of determining a catheter resistance value is also described wherein the steps are selecting the length of the distal tip of the catheter to be deflected, performing a cantilever beam test over the chosen length, and calculating the force resistance value from the catheter stiffness measurements.

Finally, a method for matching a guidewire with a compressible guide section to a catheter for precision catheter positioning is disclosed. The method requires the steps of determining the desired lumen diameter to be treated, selecting a catheter and determining the catheter resistance force, and choosing a guidewire having a guide section with an outward radial force sufficient to deflect the catheter to the lumen wall. The relationship between a catheter and a guidewire are easily understood when employing either a graphing model of the forces, or an instrument such as a portable force meter with a programmed display.

BRIEF DESCRIPTION OF THE DRAWINGS

FIG. 4B shows a schematic of the force measuring device components.

DESCRIPTION OF THE SPECIFIC EMBODIMENTS

Figure 1:
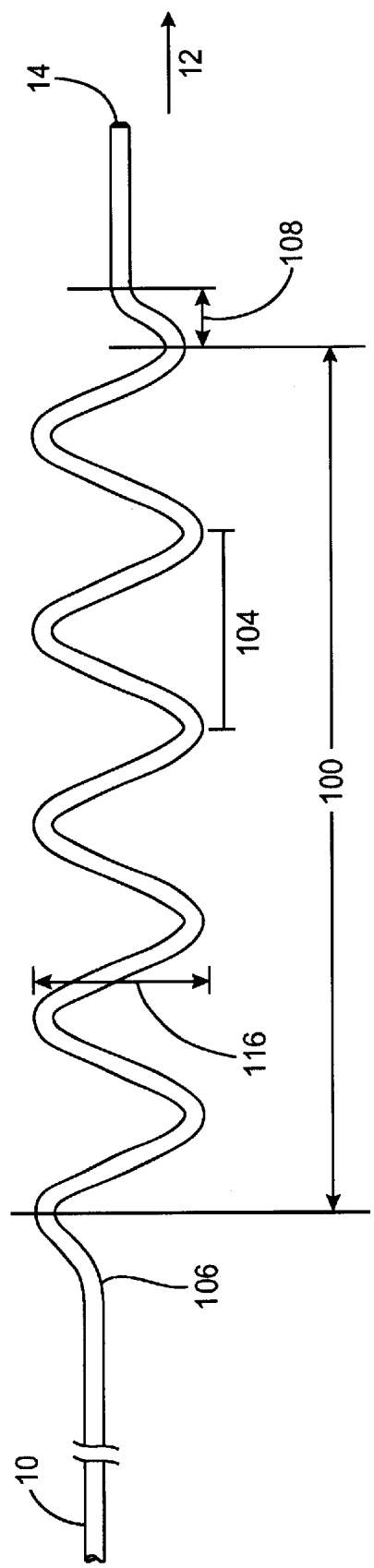
FIG. 1 is an enlarged plan view of the guide section of the present invention.
Figure 1A:
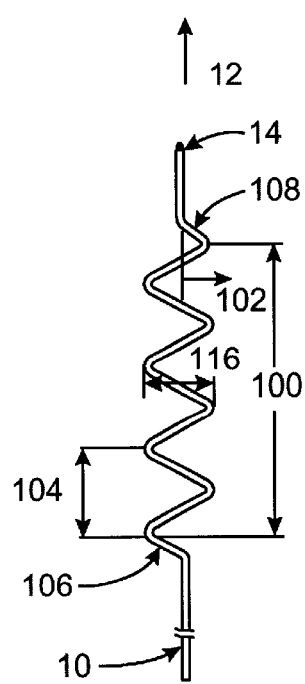
FIGS. 1A–1C show the basic embodiment of a guide section in three stages of extension.
Figure 1B:
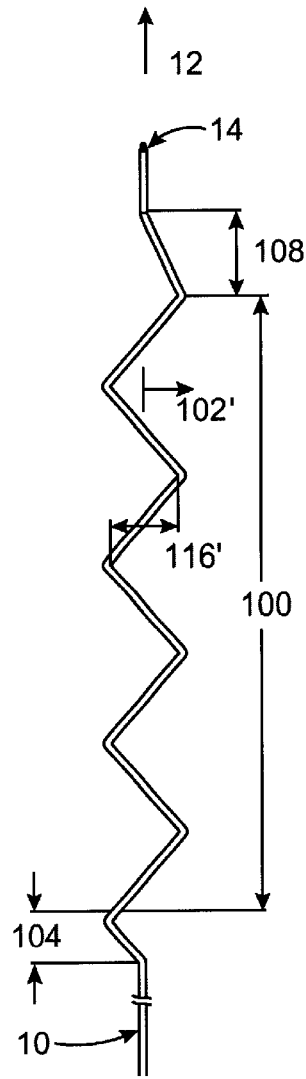
Figure 1C:
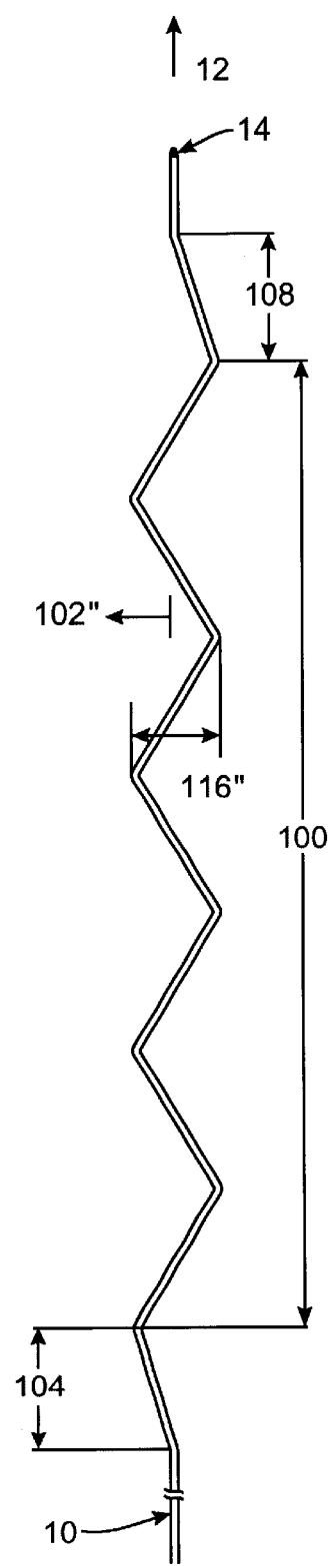

The following detailed descriptions are the best presently contemplated modes of carrying out the invention. This description is not to be taken in a limiting sense, but is made merely for the purpose of illustrating general principles of embodiments of the invention. The scope of the invention is best defined by the appended claims. In certain instances, detailed descriptions of well-known devices, compositions, components, mechanisms and methods are omitted so as to not obscure the description of the present invention with unnecessary detail.

The present invention relies heavily on a proper understanding of certain mathematical terms and physical forces. A description of the terms used herein is provided avoid confusion.

By "outward radial force" the description means a force exerted by a compressed guide section as it seeks to recover the strain it has experienced while being compressed. Typically the compression force is caused by a catheter tracking over a guidewire having a compressible guide section. As the catheter advances, local deformations immediately distal to the catheter appear on the length of the guide section. These deformations are the result of the strain the catheter exerts on the guidewire as it is advanced. The guide section seeks to resist deformation and recover the strain to return to its natural, relaxed shape. Any force the guide section exerts as it seeks to recover its natural state is an "outward radial force" with respect to the intended operation and usage of the present invention.

A "catheter resistance force" is the force the catheter exerts on the guide section. This resistive force is a result of the catheter being displaced by the guide section off of its natural axis. The catheter may be stiff or flexible in the distal end as it moves over the guidewire. The stiffer the catheter, the greater the force the catheter exerts on the guide section. Any force the catheter exerts on the guide section at the distal tip of the catheter moving forward is the "catheter resistance force" with respect to the intended operation and usage of the present invention.

The term "effective active arc length" refers to the portion of the guide section deflected by the catheter as it tracks over the guide section. The effective active arc length extends from the point at which the guide section exits the catheter to the point at which it fully contacts the lumen wall. The length of the guide section held away from the lumen wall the catheter extending from the catheter's guidewire lumen to the point of contact of the guide section with the lumen wall represents the "effective active arc length" with respect to the intended operation and usage of the present invention.

The term "effective arc angle" refers to the angle made by the effective active arc length projected onto a plane orthogonal to the major axis of the lumen. One side of the angle is defined by the line drawn from the center of the lumen to the point at which the guide section exits the catheter. The other side is defined by a line drawn from the center of the lumen to the point at which the guide section leaves the lumen wall. The effective arc angle and the effective active arc length can be experimentally derived.

A variety of physical parameters and their symbols are used in the following description, a reference table for these values is provided below.

Notation

| Symbol | Definition |
|---|---|
| $D_0$ | Diameter of guide section in its free, natural state |
| D | Diameter of guide section |
| $F_a$ | axial force |
| $F_c$ | force applied to catheter |
| $F_{GS}$ | Force the effective active arc section exerts on the catheter |
| $L_0$ | initial axial length of guide section in its free, natural state |
| $L_c$ | length of catheter in bending |
| L | axial length of guide section |
| N | number of active turns in guide section |
| P | pitch of guide section |
| $P_0$ | initial pitch of guide section in its free, natural state = initial coil spacing |
| R | radius of guide section measured from axis of guide section |
| $R_0$ | initial radius of guide section measured from axis of guide section |
| $S_{eff}$ | effective active arc length of guide section |
| $S_h$ | arc length of single wrap of guide section |
| $S_{tot}$ | total arc length of guide section |
| $w_r$ | radially directed force per unit length of the guide section |
| $\Delta D$ | change in diameter = $D_0 - D$ |
| $\Delta L$ | change in axial length of guide section = elongation = $L - L_0$ |
| $\Delta R$ | change in radius of guide section = $R_0 - R$ |
| $\delta_c$ | end displacement of catheter |
| $\delta_r$ | radial displacement |
| $\varnothing_c$ | Diameter of the catheter at its distal end |
| $\theta_{eff}$ | effective arc angle |

As used herein, "elastic" refers to the property of a material to return to its original shape after unloading. The elastic properties of most materials are limited by plastic deformation which occurs at a relatively low degree of strain. Some materials, such as spring stainless steels, will possess sufficient elasticity for at least some applications within the present invention.

As used herein, "shape memory material" refers to those materials, usually metal alloys, which return to an original shape after unloading a stress or strain amount within their elastic or super-elastic limits. These materials, often used for medical devices are well understood in the art as having the desired properties of being able to bear considerable load and still return to their original shape once the unloading has occurred. Some materials, such as certain nickel titanium alloys, e.g. Nitinol®, display both super elastic and shape memory properties and thus may be used according to more than one aspect of the present invention as described below in more detail. A nonexhaustive list of examples of shape memory materials are provided in the table below.

| Alloy | Sample Composition | Transformation-temp range (Degrees Celsius) |
|---|---|---|
| Ag—Cd | 44/49 at. % Cd | −190 to −50 |
| Au—Cd | 46.5/50 at % Cd | 30 to 100 |
| Cu—Al—Ni | 14/14.5 wt % Al 3 to 4.5 wt % Ni | |
| Cu—Sn | 15 at. % Sn | −120 to 30 |
| Cu—Zn | 38.5/41.5 wt % Zn | −180 to −10 |
| Cu—Zn—X | (X = a few wt % Si, Sn, Al) | −180 to 200 |
| In—Ti | 18/23 at % Ti | 60 to 100 |
| Ni—Al | 36/38 at. % Al | −180 to 100 |
| Ni—Ti | 49/51 at % Ni | −50 to 110 |
| Fe—Pt | 25 at % Pt | −130 |
| Mn—Cu | 5/35 at % Cu | −250 to 180 |
| Fe—Mn—Si | 32 wt % Mn, 6 wt % Si | −200 to 150 |

I. Guidewire with Guide Section Exerting an Outward Radial Force when Compressed FIG. 1 shows the preferred embodiment of the present invention. A guidewire 10 with an atraumatic tip 14 is shown with a helical guide section 100 capable of exerting an outward radial force 102 when compressed. The vectors 102, 102' and 102" represent the larger radial forces the greater the compression of the guide section 100. The guide section 100 further comprises a plurality of helical winds 104 with a proximal transition period 106 and a distal transition period 108. The guide section 100 also has a relaxed helical diameter 116 and an axis of extension 12. The guidewire 10 has a core wire 11 (see below) made of a shape memory material such as nickel-titanium or other shape memory alloy. The actual outward radial force 102 of the guide section 100 depends on the composition of the guide section 100 when it is made and the shape it is fashioned into. In general for interventional procedures the total outward radial force 102 must be sufficient to provide a force that can deflect a catheter tip 206 (see below) in a controlled manner to abut a lumen wall 202 while at the same time not damaging the lumen wall 202 the guide section 100 is placed into. The outward radial force 102 generated by a portion of a single helical wind 104 is estimated to be between 0.001 pounds and 0.5 pounds and the preferable radial force of a single wind is in the range of 0.01 pound and 0.5 pounds. The helical diameter 116 of the relaxed guide section 100 of the present invention is anywhere between 1 and 20 mm with the preferred embodiment being in the range of 2–5 mm.

The guide section 100 exerts an outward radial force 102 when compressed which is directly proportional to the axial extension of the guide section 100. The outward radial force 102 is distributed along each helical wind 104 of the guide section 100 in proportion to the radial compression of the particular wind. That is, those helical winds 104 that are more compressed than others, will have a greater outward force 102". Since it is difficult to accurately measure the force values of the guide section 100 in vivo (when it is compressed inside a body lumen), the current description uses a test model in an in vitro setting. That is a bench top test is used to determine the force values of the guide section 100. In general the guide section 100 has a maximum outward radial force 102" less than four (4) pounds per linear centimeter of the guide section 100 in its maximum compressed state. Preferably the outward radial force 102 is in between of 0.009 pounds to 2.5 pounds. The actual radial force of the guide section 100 depends on the length of the guide section 100, the proximity of the helical winds 104

(pitch), the thickness of the wire used to make the guidewire 10 and the material used in making the guidewire 10. A thicker core wire, tighter pitch and smaller helical diameter 116 are factors which contribute to increased outward radial force when the guide section 100 is compressed.

Competing factors must be considered when the guide section 100 is made. A guide section 100 having a helical diameter 116 smaller than the vessel it may operate in will not provide the necessary relationship between the guidewire 10 and catheter 200 to provide precision location of the catheter 200 in a body lumen 202. Likewise if the core wire 11 is too stiff, the guide section 100 will not deform when the catheter 200 tracks over it. In general the guide section 100 of the present invention will operate using materials generally the same as used for straight guidewires. The free state condition of the guide section 100 is characterized by measuring the diameter, pitch length, and number of active coils of the guide section 100 in its free state (i.e. unconstrained).

The use of a shape memory material in the guide section 100 allows the guide section 100 to be deformed in the elastic and super elastic range of the material and return to the original shape of the guide section 100. The inherent unloading of force, or relaxing of the guide section 100 when it is compressed, produces the outward radial force 102. The thicker the core wire 11 of the guidewire 10, the stronger the outward radial force 102, or the greater the resistance to deformation the guide section 100 possesses. The combination of elements and properties provide the guide section 100 of the guidewire 10 with an outward radial force 102 sufficient to deflect a catheter 200 into the lumen wall 202 of the patient as the catheter 200 is being advanced over the guide section 100. This relationship holds true as the helical diameter 116 of the guide section 100 compresses from its free state to conform to the lumen diameter.

Figure 2:
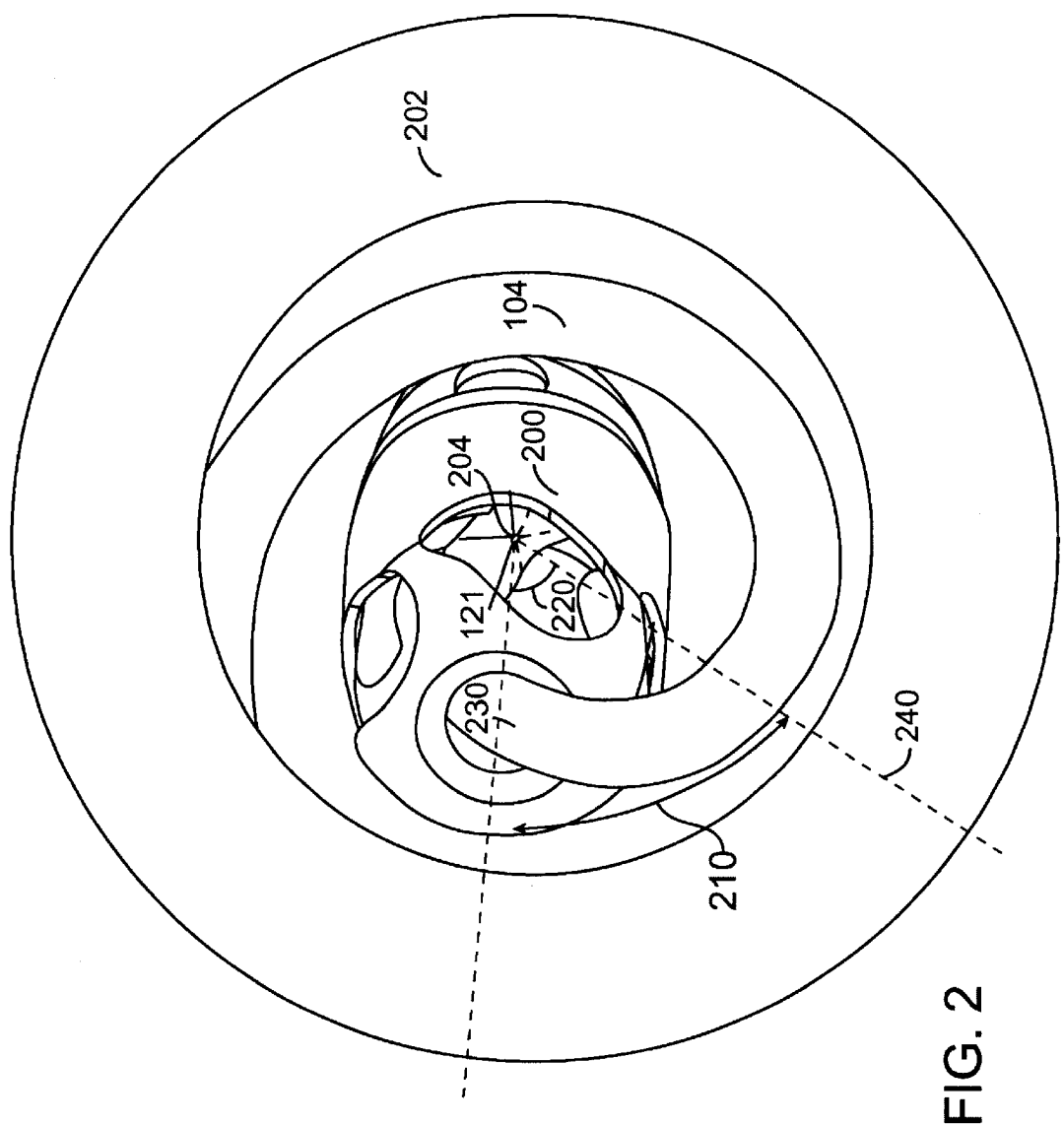
FIG. 2 shows a catheter as it advances over the guide section in a lumen.
Figure 3A:
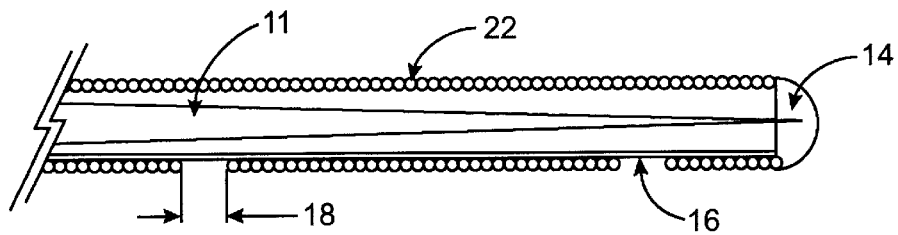
FIGS. 3A and 3B show a guide section in the form a wire acting as a spring detent.
Figure 3B:
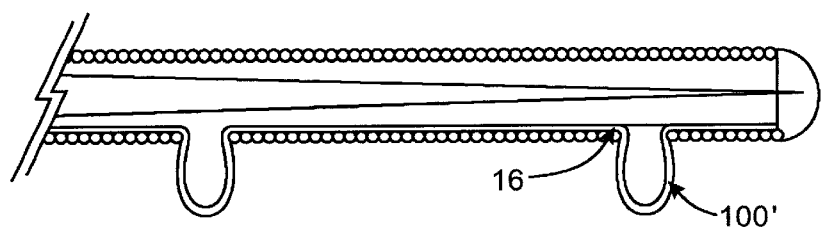
Figure 3C:
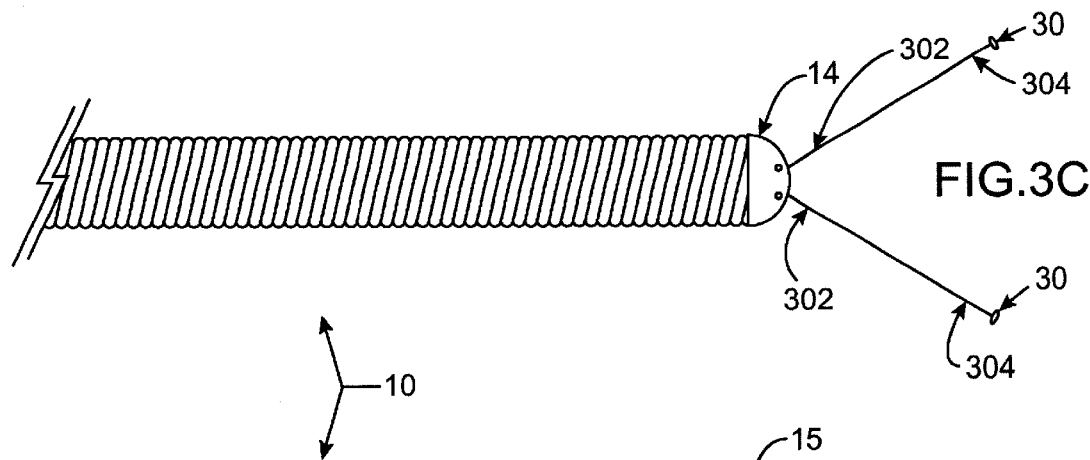
FIGS. 3C and 3D show a guide section in the form of displacement wires.
Figure 3D:
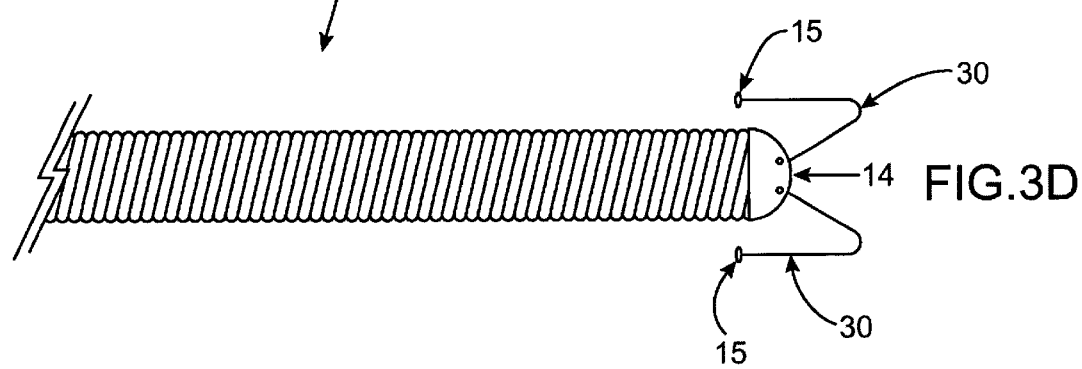

FIG. 2 illustrates the relationship between the guide section 100 and the catheter 200. When the guide section 100 and the catheter 200 are deployed against a lumen wall 202, the portion of the guide section 100 contacting the lumen wall 202 does not impart outward radial force on the catheter 200, as its outward force is being completely supported by the lumen wall 202. The portion of the guide section 100 that does impart outward radial force to the catheter 200 is that segment of the guide section 100 that is deflected off of the lumen wall 202 by the catheter 200. This segment is defined as the active arc length 210 whose length can be observed as the segment of the guide section 100 that exits the catheter 200 and continues until the guide section 100 fully re-contacts the wall of the lumen wall 202.

The effective arc angle 220 is the angle the active arc length 210 makes projected onto a plane orthogonal to the major axis 12' of the lumen. It can be observed from a frame of reference looking down the major axis 12' of the lumen. The effective arc angle 220 is the angle between a first radial line 230 defined by the center of the lumen 204 and the point at which the guide section 100 exits the catheter 200 and a second radial line 240 defined by the center of the lumen 204 and the point at which the guide section 100 fully re-contacts the lumen wall 202.

FIGS. 3A–3D show two alternative guidewires that also demonstrate the ability to provide an outward radial force sufficient to overcome the resistance force of the catheter. In the first alternative embodiment (FIGS. 3C & 3D) a guidewire 10 is provided having at least one displacement arm 30 and an atraumatic tip 14. The displacement arm 30 is a filament wire made of a shape memory alloy having a joining end 302 and a distal end 304 where the displacement arm 30 is capable of rotation of at least 180 degrees. The displacement arm tip 15 is located at the distal end 304 of each displacement arm 30 and at least one radiopaque marker (not shown) is used for determining the rotation of the displacement arm 30. The displacement arms 30 of this particular embodiment, are located at the extreme distal tip of the guidewire 10 and may be either soldered directly onto the tip of the guidewire 10 or may be included at the tip of the guidewire 10 through the use of the ball and socket joint. In operation, the displacement arms 30 have a similar bias to ensure the guidewire tip is deflected in only one direction.

The second alternative embodiment (FIGS. 3A & 3B) for the guidewire 10 is one wherein a thin lumen extends substantially through the distal end 22 of the guidewire 10. The lumen contains a filament wire 16 which is placed in parallel to the main axis 12 and parallel to the core wire 11 of the guidewire 10. The filament wire 16 has a length which is at least a little bit longer than the lumen of the distal end 22 of the guidewire 10. In this manner, the filament wire 16 can protrude through a plurality of apertures 18 are located at the distal end. As the filament wire 16 protrudes through the apertures, the wire acts as a spring detent allowing the guidewire 10 to be pushed off the lumen wall 202 and forcing the catheter 200, trapped between spring detents 100', to be in physical contact with the lumen wall 202.

The second alternative embodiment using the wire acting as a spring detent 100' is specifically designed for use with a rapid exchange catheter having a functional tip at the distal end of the catheter. The first alternative embodiment, the guidewire 10 having a displacement arm 30, can be used with either a rapid exchange catheter or a standard over-the-wire catheter.

II. Portable Force Determining Instrument

Figure 4A:
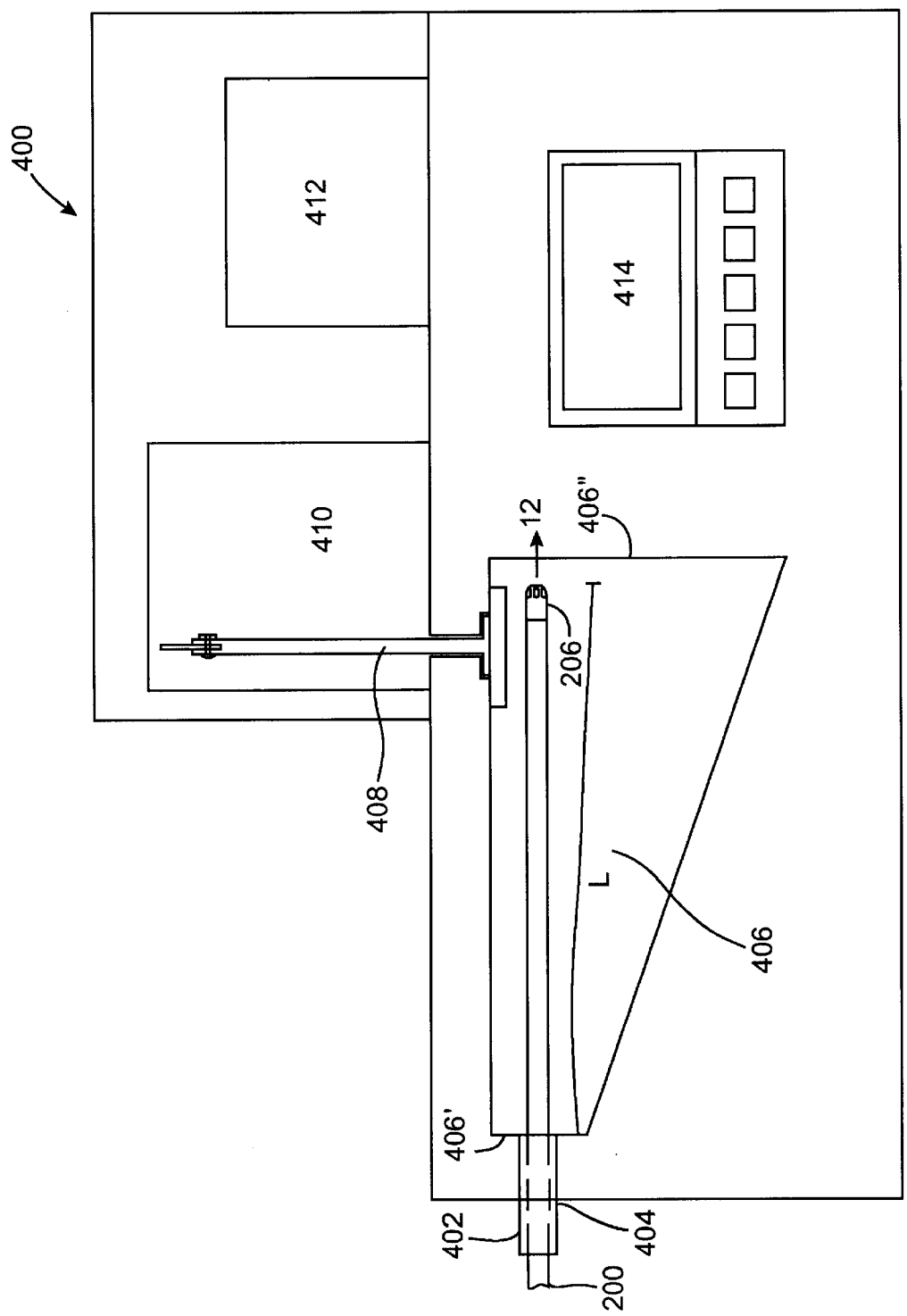
FIG. 4A is a profile view of a force measuring device.

FIGS. 4A and 4B illustrate a portable force measuring unit 400. The force measuring unit 400 of the present invention is used for determining a catheter resistance force value. The preferred embodiment is a small, hand held unit having a port 402 for receiving the distal tip 206 of a catheter 200. The receiving port 402 is generally large enough to receive any catheter 200 ordinarily used in a body lumen with an adaptable entry collar 404 which can be secured around the catheter 200 to lock it in place. The receiving port 402 leads to a test lumen 406 where the catheter distal tip 206 extends into. The catheter distal tip 206 enters at the proximal end 406' of the test lumen 406 and the distal tip 206 extends to the distal end 406" of the test lumen 406. At the distal end 406" of the test lumen 406 a deflection gauge 408 can be used to push the catheter tip 206 a precise distance off the axis 12 of the test lumen 406. A load cell 410 is connected to the deflection gauge 408 to determine the spring stiffness K of the catheter 200.

The spring stiffness K and the length of the catheter L from the fixed receiving port 402 to the deflection tip 206 are used in determining the resistance force Fc of the catheter 200. A microprocessor 412 is used to collect and interpret the data collected by the load cell 410 and the test lumen 406. A display unit 414 then indicates the catheter resistance force $F_c$ value for use in matching an appropriate guidewire 10 to the catheter 200 as described below.

III. Method of Determining Outward Radial Force of a Guide Section

A method of determining the outward radial force of the guide section 100 comprises performing an axial force deflection test and recording dimensional changes. An axial pull force test is performed to generate discrete axial force and displacement measurements of the guide section 100. The change in diameter of the guide section 100 at each of these discrete points is measured. The outward radial force 102 of the guide section 100 is calculated from these measured values.

Using measured values of the pitch and diameter of the guide section in its free state, the length of the arc of a single wrap of the guide section 100 is calculated using the following equation:

$$S_h = \sqrt{(\pi D_0)^2 + P_0^2}$$

One of the key relationships developed that relate the force relationship between the guide section 100 and the catheter 200 is the effective active arc length $S_{eff}$ and effective arc angle $\theta_{eff}$. A mathematical description of the effective active arc length ($S_{eff}$) as a function of the diameter of the guide section (D) is then developed. This may be accomplished by deploying the catheter and guide section into lumens of varying diameter and measuring and recording the diameter and effective arc angle ($\theta_{eff}$) for each lumen. Because the diameter of the guide section is the same as the diameter of each lumen, the mathematical relationship can then be determined for $\theta_{eff}$ as a function of the diameter of the guide section using appropriate curve fitting algorithms.

The total arc length of the guide section over its entire length ($S_{tot}$) is given by:

$$S_{tot} = nS_h$$

The effective radial force of the guide section is determined by first measuring the axial force, axial displacement, and radial displacement while extending the guide section axially. The axial force is measured by placing the guide section in a force-displacement measuring instrument, e.g., Instron, 5543 using a 10-pound load cell. Using a standard axial force displacement test, the load cell of the Instron is slowly moved apart so that the guide section of the guidewire is slowly stretched. The Instron can be programmed to measure on an incremental basis the force required to stretch the guide section. For example, if the Instron is set to stretch the guide section at a rate of 1 cm per minute, it can be instructed to take a force measurement every millimeter or every six seconds. Once the guide section is extended to a point such that the diameter of the guide section is smaller than the diameter of the catheter, the test should be stopped.

Alternatively, following completion of the axial force and displacement testing, the guide section may be removed from the Instron and the change in diameter of the guide section may be measured using an optical measurement device as the guide section is displaced axially. The change in diameter should be recorded at axial displacements corresponding to those at which the displacement and force measurements were taken.

Using the experimental setup described above, we can exert an axial force on the guide section over substantially its full range of deflection. For example, when measuring a 1 cm length guide section, use 10–50 discrete deflections. At each deflection, measure and record the axial displacement, axial force and diameter of the guide section. At each discrete deflection using the values recorded above, calculate the following:

1) The total axial displacement from its free state $\Delta L$ given by:

$$\Delta L = L - L_o$$

2) The change in the radius from its free state $\Delta R$ given by:

$$\Delta R = R_o - R = \frac{(D_o - D)}{2}$$

3) The outward radial force per unit length along the guide section given by:

$$w_r = \frac{F_a \Delta L}{S_{tot} \Delta R}$$

4) $\theta_{eff}$ from the relationship developed as described above.

5) The effective arc length of the helix actively transferring force to the catheter given by the equation:

$$S_{eff} = \frac{\theta°_{eff}}{360} S_h$$

6) The radial force exerted on the catheter by the guide section given by the equation:

$$F_{GS} = S_{eff} W_r$$

To account for the fact that for any $\Delta R$ of the guide section, the effective active arc length has an additional radial displacement ranging from 0 to ½ $\emptyset_c$ over its length when graphing the effective force of the guide section on the catheter translate the effective $\Delta R$ of the active arc length by $-\frac{1}{4} \emptyset_c$ relative to $\Delta R$ of the guide section as a whole.

IV. Method of Determining Resistance Force of a Catheter

A method of determining the radial deflection of a catheter comprising the steps of: First, suspending a catheter tip in a force measuring device; second, deflecting the catheter tip off axis to a pre-determined distance; third, measuring the force corresponding to the deflection of the catheter tip.

The resistance force a catheter ($F_c$) exerts on the guide section is the force necessary to deflect the distal end of the catheter off its axis. That is, the guide section must exert sufficient force on the catheter to force the catheter to follow the desired path of the guide section. The resistance force of the catheter ($F_c$) can be determined by using a cantilever beam stiffness test [See FIG. 4] with the catheter used as the beam. A force applied to the cantilever beam deflects the beam off of its natural axis.

In practice, when using a catheter in a body lumen, the maximum distance that the catheter can be deflected is determined by the diameter of that lumen. The distance the catheter will be deflected in use in a body lumen is estimated to be between 0.5 mm and 5 mm. The specific maximum deflection can be determined by the greatest radius of the largest guide section intended for use with this catheter. The effective beam length of the catheter being used in a body lumen varies depending on the body lumen in which the catheter is inserted. In the tortuous anatomy of the coronary arteries the effective beam length of the catheter may be short. However, if the catheter is inserted into a straight lumen, the effective beam length of the catheter will be longer. Here, the effective beam length of the catheter in use is estimated to be between 1 cm and 5 cm.

The intent of the cantilever beam test is to model the effective beam length of the catheter in use. As discussed above, determining an effective beam length that models the actual use of the catheter is difficult. The beam length of the catheter in the cantilever beam test should best be determined based on its specific usage. Because the stiffness of a beam increases inversely with length, a limit on the minimum length of the catheter used during the cantilever beam test is defined. For definition purposes in the present invention, it will be defined that the minimum beam length of the catheter will be that distance that the catheter can be deflected in the largest lumen expected for use from the center axis of the lumen to the lumen wall without permanent deformation to the catheter. The maximum deflection distance is defined as the largest radius of the largest guide section intended for use with the catheter.

As mentioned above, the beam length of the catheter during the cantilever beam test will be determined based on the specific use of the device. But it should be apparent to one of ordinary skill in the art that if the distal tip of the catheter is a rigid section, the resistance value of the catheter could exceed the outward force of the guide section. Should the minimum deflection required above result in permanent deformation to the tip of the catheter during the cantilever beam test, that beam length is too short to be a representative model of the catheter in actual use.

To determine the resistance force of the catheter relative to the outward force of the guide section, the resistance force of the catheter will be measured and the deflection of the catheter will be expressed as an equivalent $\Delta R$ of the guide section. To measure the force of the catheter, mount the catheter in an instrument capable of measuring force and deflection, e.g. an Instron, with the catheter having an effective beam length L discussed above. The test catheter must be prepared such that its stiffness will be that seen during its use, e.g. if the guide section passes through a lumen in the catheter during use, the guide section must be inserted into the test catheter prior to testing in such a way that the guide section contributes to the stiffness of the catheter but does not externally restrict the deflection of the catheter. Measure and record the force required to deflect the catheter orthogonal to its major axis from zero deflection (its natural, free state) to a deflection at a minimum equal to the greatest free state radius of the largest guide section intended for use with this catheter. To express the deflection of the catheter in terms of the $\Delta R_F$ of the guide section, use the following transformation:

$$R = \delta_c + \frac{1}{2}\phi_c$$

The measured deflection of the catheter can then be expressed in terms of $\Delta R$ of the guide section using:

$$\Delta R = R_0 - R = R_o - (\delta_c + \frac{1}{2}\phi_c)$$

V. Method of Matching a Catheter and Guidewire

Detailed methods have determined the radial deflection of the catheter, the outward radial force of the guide section, and providing the determination met by the interrelation between outward radial force of the guide section and the catheter resistance are provided in detail as follows: A method of determining if the catheter can be deflected by a guidewire having a compressible guide section so that the catheter tip will remain in contact with the lumen wall as the catheter is advanced over the guide section. This method comprises the steps of graphing the force the guide section exerts on the catheter and the resistive force of the catheter as a function of $\Delta R$ of the guide section.

It can be appreciated that if the area under the curve of the radial force of the guide section is integrated, less the integrated area under the curve of the force value of the catheter, the entire domain between the two lines represents the deflection force, which the guide section provides, which is the subject of the present invention. Generally, the present invention operates with a outward radial force for the entire guide section of less than 8 pounds. Preferably, the operable range of the guide section is between 0.09 and 2.5 pounds.

What is claimed is:

1. A method of matching a catheter to a guidewire for a medical procedure requiring precision radial positioning comprising the steps of:

(a) determining a lumen diameter of a body lumen to be treated;

(b) selecting a catheter to be used in said body lumen;

(c) choosing the effective length of said catheter;

(d) measuring a catheter resistance value of said catheter over said effective length; and (e) matching a guidewire having a compressible guide section to said catheter resistance value to ensure said guidewire has sufficient outward radial force when compressed to deflect said catheter into said lumen wall.

2. The method of claim 1, wherein step (d) further comprises measuring the beam stiffness in a portable force measuring device and converting the beam stiffness of said catheter into said catheter resistance value.

3. The method of claim 1, wherein step (e) further comprises graphing the catheter resistance value against the outward radial force of a guidewire for verification of compatibility between said guidewire and said catheter for precise radial positioning further comprising the steps of:

(a) graphing the radial force of the guide section as a function of the change in radius of the guide section as it is stretched; and (b) overlaying the resistance force of the catheter after converting the measured values of the catheter resistance force into the same coordinate system as that used by the guide section of the guidewire.

* * * * *